(12) United States Patent
Koinuma et al.

(10) Patent No.: US 8,047,078 B2
(45) Date of Patent: Nov. 1, 2011

(54) FLAW DETECTION TESTING METHOD

(75) Inventors: Hiroaki Koinuma, Yokohama (JP); Koji Matsuyama, Yokohama (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 361 days.

(21) Appl. No.: 12/464,654

(22) Filed: May 12, 2009

(65) Prior Publication Data

US 2009/0320600 A1 Dec. 31, 2009

(30) Foreign Application Priority Data

Jun. 26, 2008 (JP) ................................. 2008-167610

(51) Int. Cl.
*G01N 29/04* (2006.01)
(52) U.S. Cl. ........................................... 73/600; 73/627
(58) Field of Classification Search ......................... None
See application file for complete search history.

(56) References Cited

U.S. PATENT DOCUMENTS

| | | | | |
|---|---|---|---|---|
| 5,442,286 A * | 8/1995 | Sutton et al. | ................... | 324/242 |
| 5,558,500 A * | 9/1996 | Elliott et al. | ............... | 416/220 R |
| 6,745,622 B2 * | 6/2004 | Smith et al. | ................. | 73/112.01 |
| 7,026,811 B2 * | 4/2006 | Roney et al. | ................... | 324/242 |
| 7,579,830 B2 * | 8/2009 | Roney et al. | ................... | 324/238 |
| 2003/0221497 A1* | 12/2003 | Murphy et al. | .............. | 73/865.9 |
| 2004/0083801 A1* | 5/2004 | Smith et al. | ................. | 73/119 R |
| 2006/0280604 A1* | 12/2006 | Roney et al. | .................... | 416/61 |
| 2007/0089545 A1* | 4/2007 | Roney et al. | ................. | 73/865.8 |

FOREIGN PATENT DOCUMENTS

JP   2001-116728 A   4/2001

* cited by examiner

*Primary Examiner* — Andre Allen
(74) *Attorney, Agent, or Firm* — Ohlandt, Greeley, Ruggiero & Perle, L.L.P.

(57) ABSTRACT

There is provided a flaw detection testing method applied to a slot dovetail portion of a turbine generator rotor shaft. The flaw detection testing method includes an angle determining step of determining a slot angle of the slot dovetail portion using a variable-angle ultrasonic probe, a flaw detection performing step of, on the basis of a determination result in the angle determining step, using an angle ultrasonic probe or a phased array probe to perform flaw detection to detect a flaw in the slot dovetail portion, and a flaw depth measuring step of, when the flaw is detected in the flaw detection performing step, using an angle ultrasonic probe to measure a depth of the flaw from a surface of the slot dovetail portion.

7 Claims, 12 Drawing Sheets

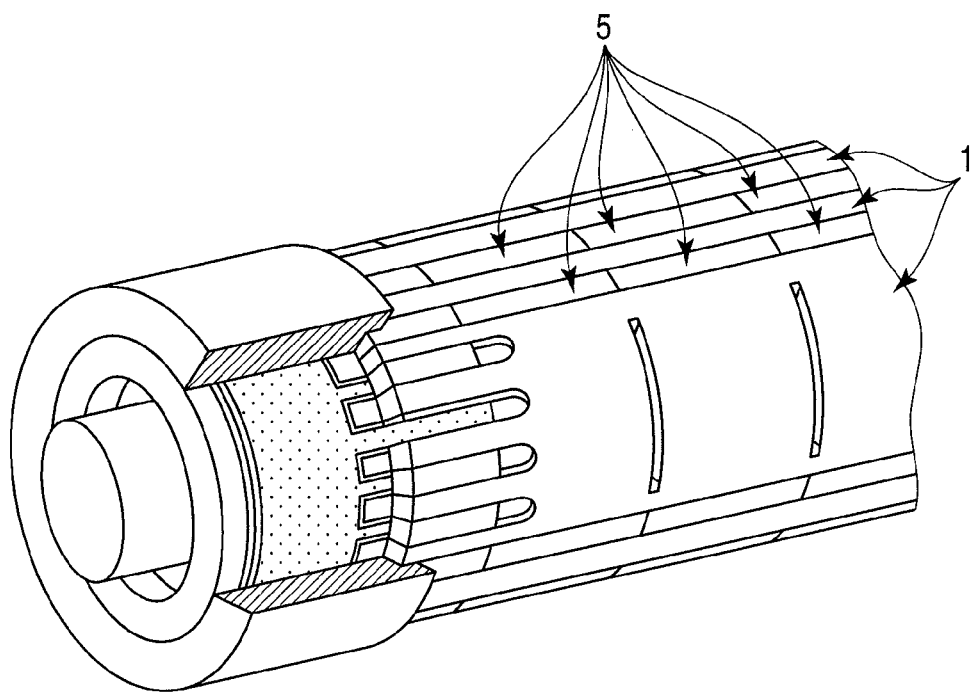
F I G. 3
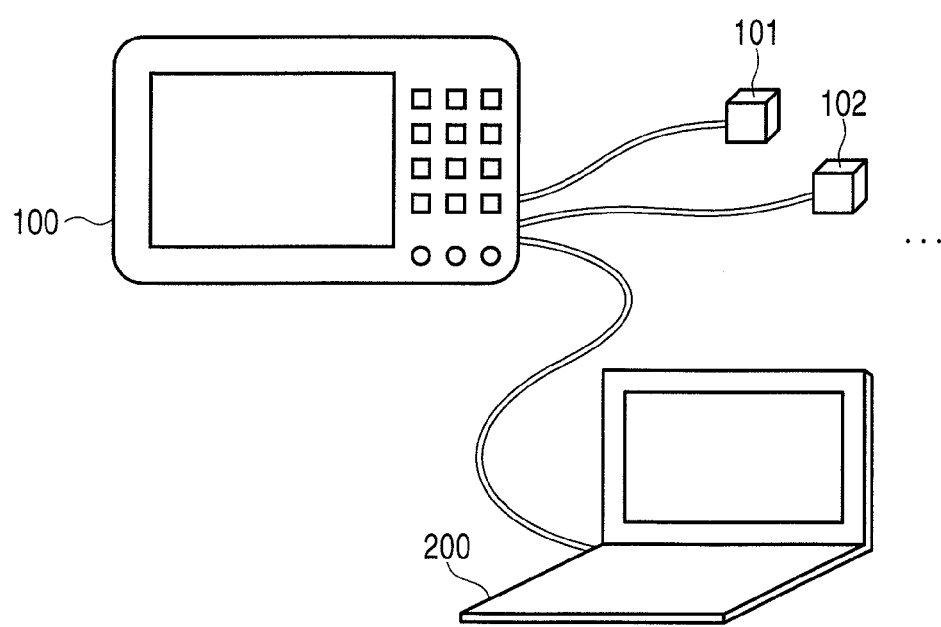
F I G. 4

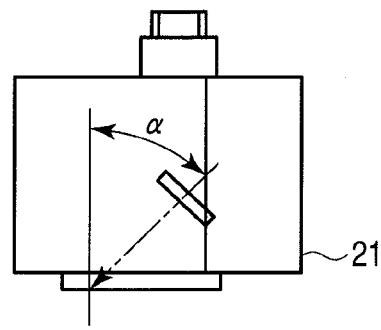 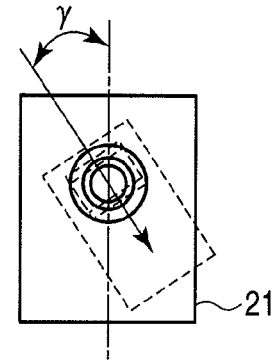
FIG. 11A    FIG. 11B
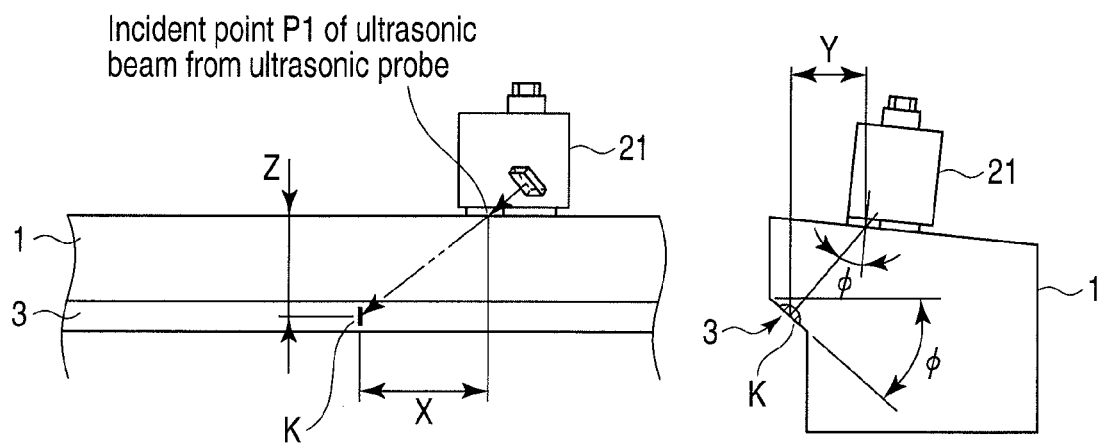
FIG. 12A    FIG. 12B

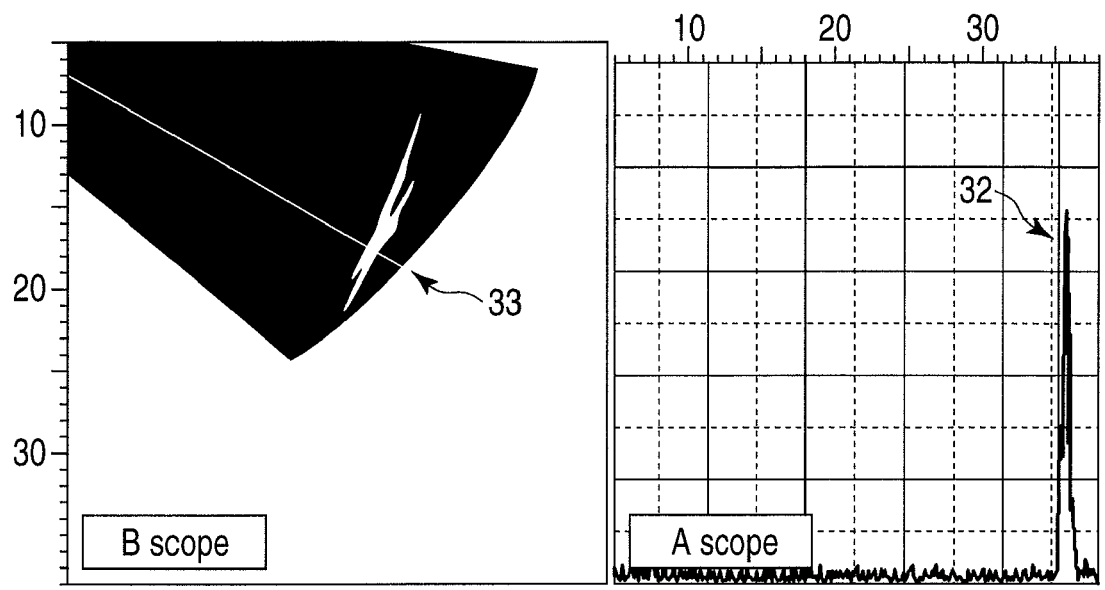
F I G. 17
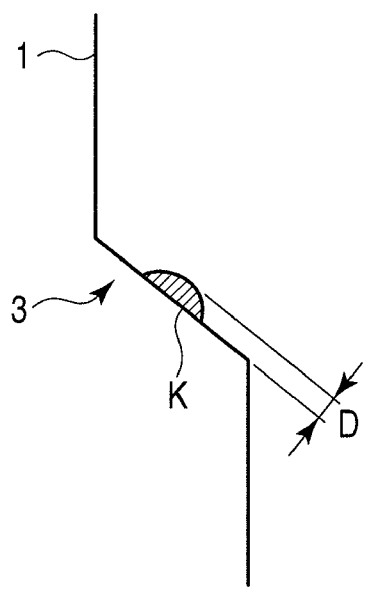
F I G. 18

FLAW DETECTION TESTING METHOD

CROSS-REFERENCE TO RELATED APPLICATIONS

This application is based upon and claims the benefit of priority from prior Japanese Patent Application No. 2008-167610, filed Jun. 26, 2008, the entire contents of which are incorporated herein by reference.

BACKGROUND OF THE INVENTION

1. Field of the Invention

The present invention relates to a flaw detection testing method applied to a slot dovetail portion of a turbine generator rotor shaft.

2. Description of the Related Art

While a turbine generator rotor is in operation, a fretting fatigue fracture may occur in a slot dovetail portion of a turbine generator rotor shaft, that is, a shaft side of the vicinity of a shoulder portion of a rotor coil wedge to be inserted.

Known methods for detecting the fretting fatigue fracture during a periodic inspection are magnetic particle testing and eddy current testing, in which surface flaw detection is performed with an end ring and the rotor coil wedge disassembled.

However, to allow the end ring and the rotor coil wedge to be disassembled, the rotor needs to be carried to a manufacturing plant. This increases a period during which a power plant needs to be shut down, placing a heavy burden on power companies. Thus, ultrasonic testing is often adopted, which is an internal flaw detection technique that can be performed at the site without the need for disassembling.

When ultrasonic testing is applied to the slot dovetail portion, the slot angle of the slot dovetail portion to an outer peripheral surface of the rotor shaft, which is a test surface, needs to be taken into account.

The slot angle is known if a manufacturing drawing of the rotor shaft 1 is available. Otherwise, the slot angle needs to be pre-measured in order to allow an ultrasonic probe to be selected.

Furthermore, to increase the accuracy of detection of flaws such as the fretting fatigue fracture, which generally have small opening widths and which are directional, a reflection angle at which an ultrasonic beam is reflected by the flaw needs to be adjusted so as to avoid mode conversion losses in spite of the constraint on the slot angle.

If any flaw is detected, the depth of the flaw needs to be measured in order to determine whether operation can be continued or repairs are required.

BRIEF SUMMARY OF THE INVENTION

Accordingly, it is an object of the present invention to provide a flaw detection testing method that enables ultrasonic testing to be efficiently carried out on a slot dovetail portion of a turbine generator rotor shaft.

According to one aspect of the present invention, there is provided a flaw detection testing method applied to a slot dovetail portion of a turbine generator rotor shaft, the method comprising: an angle determining step of determining a slot angle of the slot dovetail portion using a variable-angle ultrasonic probe; a flaw detection performing step of, on the basis of a determination result in the angle determining step, performing flaw detection to detect a flaw in the slot dovetail portion using an angle ultrasonic probe or a phased array probe; and a flaw depth measuring step of, when the flaw is detected in the flaw detection performing step, measuring a depth of the flaw from a surface of the slot dovetail portion using an angle ultrasonic probe.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 3 is a perspective view showing an example of the appearance of the rotor shaft 1 in which the rotor coils 4 and rotor coil wedges 5 shown in FIG. 2 are installed;

FIG. 4 is a diagram showing an example of devices used for the flaw detection testing according to the embodiment;

FIGS. 11A and 11B are diagrams showing the incident angle $\alpha$ and inclination $\gamma$ relating to a shear-wave angle ultrasonic probe 21 used for slot dovetail portion flaw detection S2;

FIGS. 12A and 12B are diagrams showing the positional relationship between the shear-wave angle ultrasonic probe 21 and a flaw K as viewed in the directions of a y axis and an x axis;

FIG. 17 is a diagram showing a sectorial flaw detection image and a waveform obtained on the screen of the ultrasonic flaw detector 100 during the slot dovetail portion flaw detection S2;

FIG. 18 is a diagram illustrating a flaw depth D from a surface of the slot dovetail portion 3;

DETAILED DESCRIPTION OF THE INVENTION

Embodiments of the present invention will be described below with reference to the drawings.

Figure 1:
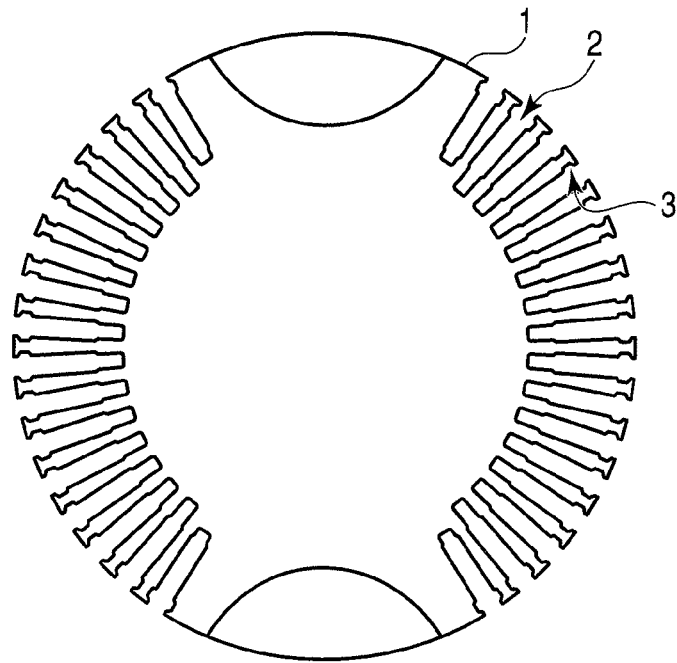
FIG. 1 is a sectional view showing an example of a core portion of a turbine generator rotor shaft 1 having a slot dovetail portion to be tested by a flaw detection testing method according to an embodiment of the present invention.

FIG. 1 is a sectional view showing an example of a core portion of a turbine generator rotor shaft having a slot dovetail portion to be tested by a flaw detection testing method according to an embodiment of the present invention.

As shown in FIG. 1, a rotor shaft 1 has a plurality of slots 2 in which rotor coils and rotor coil wedges (not shown in the drawings) are to be installed. The rotor shaft 1 also has slot dovetail portions 3 with which shoulder portions of the rotor coil wedges contact when the rotor coils and the rotor coil wedges are installed in the slots 2.

Figure 2:
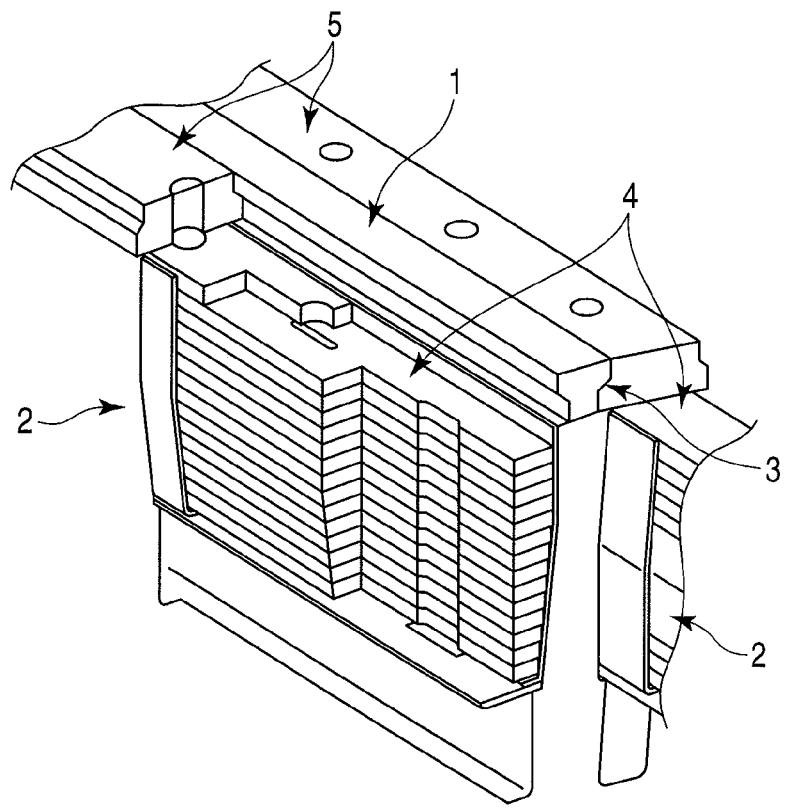
FIG. 2 is a perspective view showing an example of a structure in which rotor coils 4 and rotor coil wedges 5 are installed in slots 2 in the rotor shaft 1 shown in FIG. 1.

FIG. 2 is a perspective view showing an example of a structure in which rotor coils 4 and rotor coil wedges 5 are installed in slots 2 in the rotor shaft 1 shown in FIG. 1. FIG. 3 is a perspective view showing an example of the appearance of the rotor shaft 1 in which the rotor coils 4 and rotor coil wedges 5 shown in FIG. 2 are installed.

As shown in FIGS. 2 and 3, each of the rotor coils 4 is inserted into the corresponding one of the slots 2 in the rotor shaft 1. The rotor coil 4 is fixed by the corresponding one of the rotor coil wedges 5. At this time, a slot dovetail portion 3 contacts with a shoulder portion of the rotor coil wedge 5. Thus, while the rotor is in operation, a fretting fatigue fracture may occur in the slot dovetail portion 3. In the present embodiment, flaw detection testing is carried out on such a flaw with the rotor coils 4 and the rotor coil wedges 5 remaining installed.

FIG. 4 is a diagram showing an example of devices used for the flaw detection testing according to the present embodiment.

The present embodiment uses an ultrasonic flaw detector 100, various ultrasonic probes (including a phased array probe) 101, 102, . . . , an information processing device (computer, an information portable terminal, or the like) 200, and the like.

The ultrasonic flaw detector 100 is a device that carries out ultrasonic flaw detection testing on a target such as the slot dovetail portions 3 or the like in the rotor shaft 1, through ultrasonic probes 101, 102, . . . . The information processing device 200 performs various calculations (calculations of angles, sizes, and the like) required for the testing.

Figure 5:
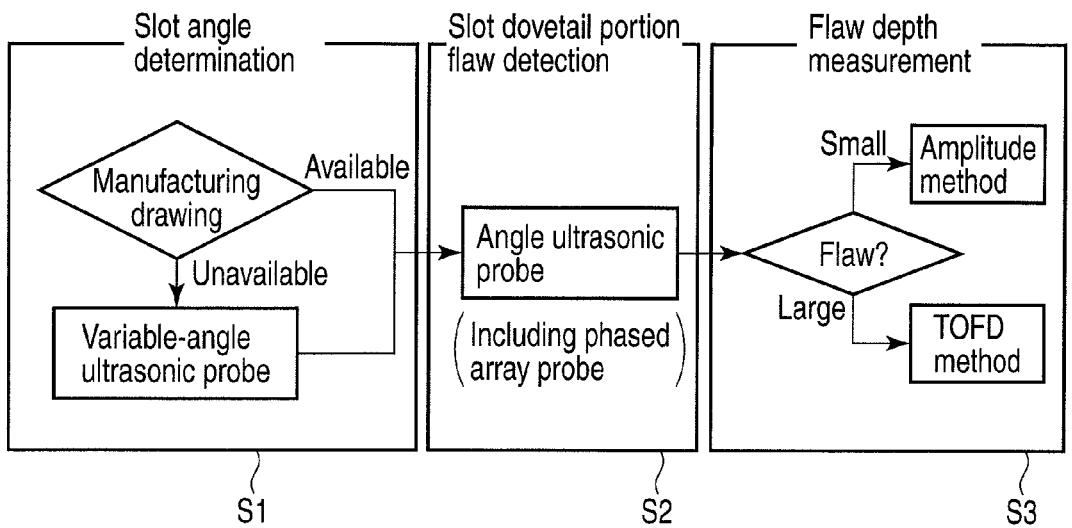
FIG. 5 is a diagram showing an example of a process procedure constituting the flaw detection testing method according to the embodiment.

FIG. 5 is a diagram showing an example of a process procedure constituting the flaw detection testing method according to the present embodiment.

In the present embodiment, the ultrasonic flaw detection testing is carried out on the slot dovetail portion 3 in order of slot angle determination (angle determining step) S1, slot dovetail portion flaw detection (flaw detection performing step) S2, and flaw depth measurement (flaw depth measuring step) S3.

In the slot angle determination S1, the slot angle (inclination) of the slot dovetail portion 3 is determined. First, whether or not a manufacturing drawing is available is checked. At this time, whether or not the desired manufacturing drawing is available may be checked, for example, on the basis of information pre-registered in a recording medium in the information processing device 200. If the manufacturing drawing is available, the slot angle of the slot dovetail portion 3 is determined from the drawings. If the manufacturing drawing is unavailable, a variable-angle ultrasonic probe is used to measure the slot angle of the slot dovetail portion 3. Various calculations required in this case can be performed by the information processing device 200.

In the slot dovetail portion flaw detection S2, on the basis of the determination results obtained in the slot angle determination S1, the flaw detection to detect a flaw in the slot dovetail portion 3 is performed using an angle ultrasonic probe or a phased array probe.

In the flaw depth measurement S3, if any flaw is detected as a result of the slot dovetail portion flaw detection S2, the depth of the flaw is measured using an angle ultrasonic probe. Here, if the size of the flaw detected by the slot dovetail portion flaw detection S2 is smaller than a preset value, the depth of the flaw is measured by an amplitude method utilizing the relationship between the depth of the flaw and the amplitude of a reflection echo obtained from the flaw. On the other hand, if the size of the flaw detected by the slot dovetail portion flaw detection S2 is equal to or greater than the preset value, the depth of the flaw is measured by a time of flight diffraction (TOFD) method.

The slot angle determination S1, the slot dovetail portion flaw detection S2, and the flaw depth measurement S3 will be sequentially described below in detail.

(Slot Angle Determination)

With reference to FIGS. 6 to 9, the slot angle determination S1 will be described. The slot angle is known if a manufacturing drawing of the rotor shaft 1 is available. Otherwise, the slot angle is pre-measured in order to select the ultrasonic probe.

Figure 6:
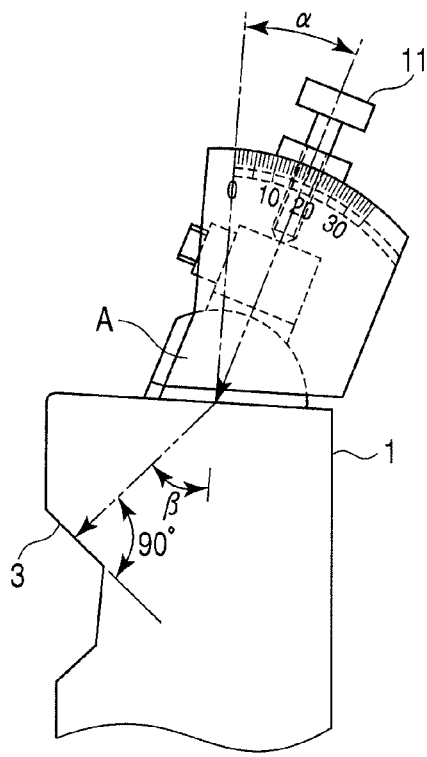
FIG. 6 is a diagram showing detection of a reflection echo corresponding to an ultrasonic beam which is emitted by a longitudinal-wave variable-angle ultrasonic probe 11 installed on an outer peripheral surface of the rotor shaft 1 and which is then reflected by a slot dovetail portion 3.
Figure 7:
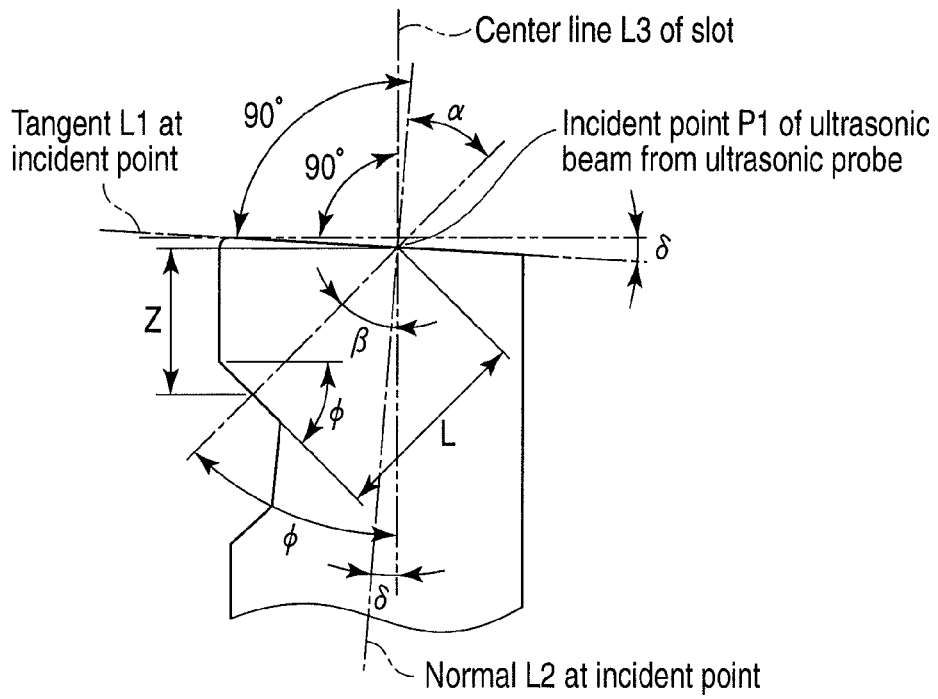
FIG. 7 is a diagram showing various parameters used to measure the slot angle of the slot dovetail portion 3.

FIG. 6 is a diagram showing detection of a reflection echo corresponding to an ultrasonic beam which is emitted by a longitudinal-wave variable-angle ultrasonic probe 11 installed on an outer peripheral surface of the rotor shaft 1 and which is then reflected by the slot dovetail portion 3. FIG. 7 is a diagram showing various parameters used to measure the slot angle of the slot dovetail portion 3. In FIGS. 6 and 7, α denotes an ultrasonic (longitudinal wave) incident angle, β denotes an ultrasonic (shear wave) refractive angle, and δ denotes the curvature angle of a test surface. Furthermore, φ denotes the slot angle, L denotes a beam path length, and Z denotes the depth of the slot dovetail portion.

In the slot angle measurement, the slot angle φ of the slot dovetail portion 3 and the slot dovetail portion depth Z are calculated on the basis of the ultrasonic incident angle α and beam path length L at which a reflection echo corresponding to an ultrasonic beam which is emitted by the longitudinal-wave variable-angle ultrasonic probe 11 and which is then reflected by the slot dovetail portion 3 has the maximum amplitude.

There are relationships expressed by Calculation Formulae (1) to (3) among the parameters.

$$\beta = \sin^{-1}\{(5900/2730)\sin\alpha\} \quad (1)$$

$$\phi = \beta + \delta \quad (2)$$

$$Z = L\cos\phi \quad (3)$$

Figure 8:
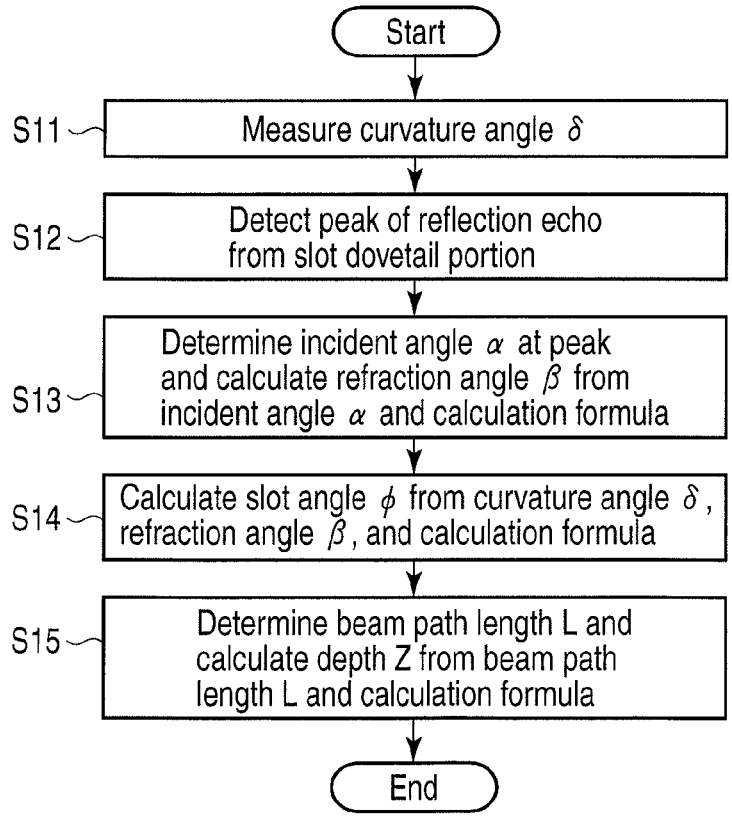
FIG. 8 is a flowchart showing the details of a process procedure of measuring the slot angle.

Now, the process procedure of the slot angle measurement will be described in detail with reference to FIG. 8. First, the curvature angle δ is measured with a protractor (step S11).

The curvature angle δ is the angle between a normal to a tangent L1 located on a shaft surface at an incident point 21 at which an ultrasonic beam is incident on the rotor shaft 1 and a line L3 (a center line of the slot), in a depth direction, of the rotor coil wedge and rotor coil contacting with the slot dovetail portion 3.

Then, a peak of a reflection echo from the slot dovetail portion 3 is detected (step S12).

Figure 9:
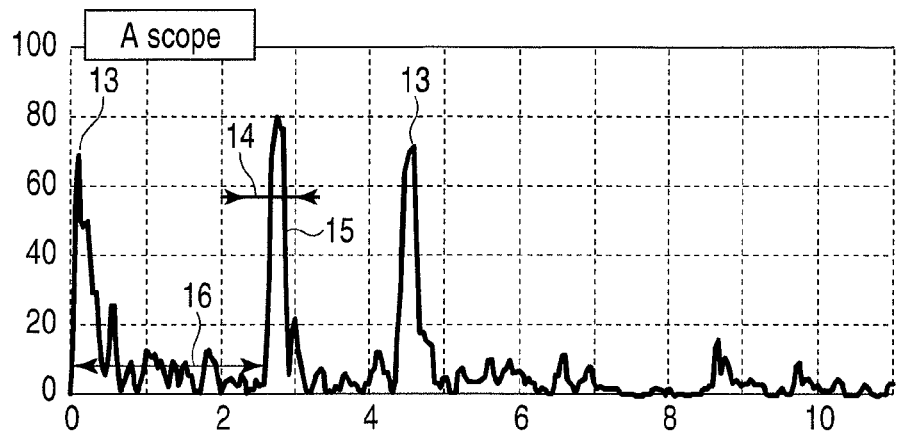
FIG. 9 is a diagram showing a waveform obtained on a screen of an ultrasonic flaw detector 100 during measurement of the slot angle.

For example, such a waveform as shown in FIG. 9 is obtained on the screen of the ultrasonic flaw detector 100 in an A scope (the axis of abscissa: time or distance, the axis of ordinate: echo height). That is, a period 14 in which a reflection echo from the slot dovetail portion 3 appears is present between two peaks 13 of multiple reflections from a test surface in an acrylic resin A shown in FIG. 6. A peak 15 during the period 14 is detected.

Then, the incident angle α at the peak 15 is determined from a probe scale. The refraction angle D is calculated from the incident angle α and Calculation Formula (1) (step S13).

Then, the slot angle φ is calculated from the curvature angle δ, the refraction angle β, and Calculation Formula (2) (step S14).

Finally, the beam path length L is determined on the basis of the screen of the ultrasonic flaw detector 100. The slot dovetail portion depth Z is calculated from the beam path length L, the slot angle φ, and Calculation Formula (3) (step S15). The slot dovetail portion depth Z is utilized as a reference for a position where the ultrasonic probe used in the slot dovetail portion flaw detection S2, described below, is installed.

For example, the beam path length L corresponding to the period 16 from the first reflection (the first one of the two peaks 13) from the test surface to the peak 15 is calculated on the basis of the waveform shown in FIG. 9.

(Slot Dovetail Portion Flaw Detection)

The slot dovetail portion flaw detection S2 will be described with reference to FIGS. 10 to 17.

Figure 10:
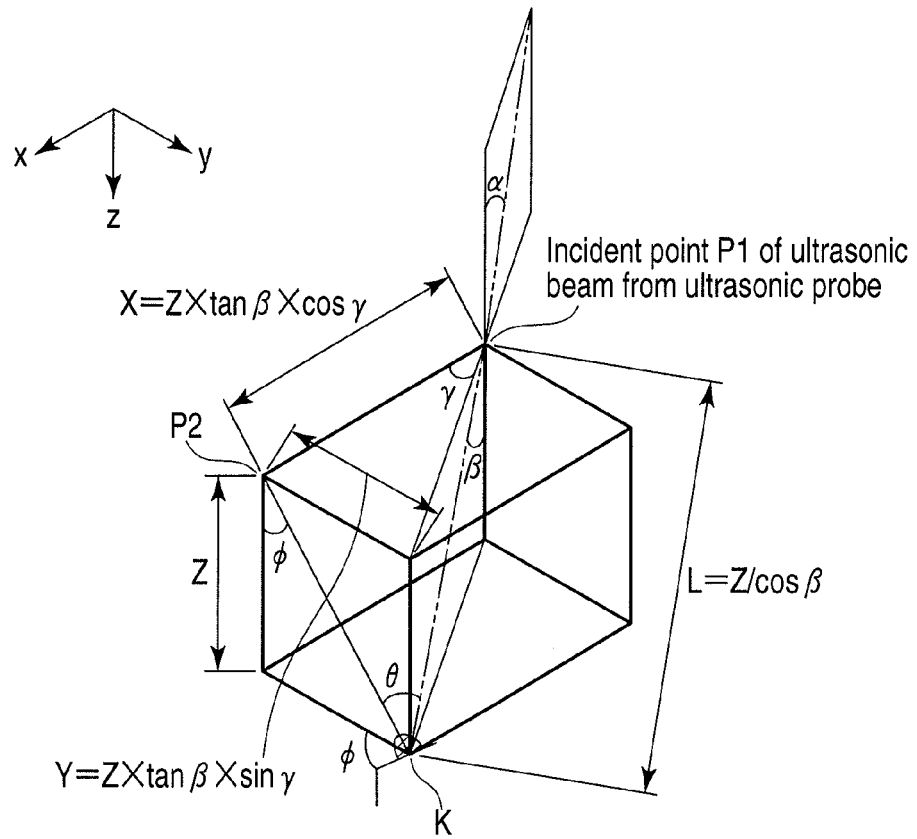
FIG. 10 is a diagram showing various parameters used to set the angle $\theta$ of reflection from a flaw in the slot dovetail portion 3, an ultrasonic incident angle $\alpha$, the inclination $\gamma$ of the ultrasonic probe.

FIG. 10 is a diagram showing various parameters used to set the angle of reflection from a flaw in the slot dovetail portion 3, the ultrasonic incident angle, and the inclination of the ultrasonic probe. In FIG. 10, γ denotes the inclination as viewed from an upper part of the probe, θ denotes the angle of reflection from the flaw, X denotes the axial distance of the slot dovetail portion, and Y denotes the circumferential distance of the slot dovetail portion. α, β, δ, φ, L, and Z have already been described with reference to FIG. 7. FIGS. 11A and 11B are diagrams showing the incident angle α and inclination γ relating to the shear-wave angle ultrasonic probe 21 used for the slot dovetail portion flaw detection S2. FIGS. 12A and 12B are diagrams showing the positional relationship between the shear-wave angle ultrasonic probe 21 and the flaw K as viewed in the directions of a y axis and an x axis.

In the slot dovetail portion flaw detection S2, for preparation for the actual flaw detection of the slot dovetail portion 3, the reflection angle θ at which an ultrasonic beam from the shear-wave angle ultrasonic probe 21, installed on the outer peripheral surface of the rotor shaft 1, is reflected by the flaw K is adjusted to a predetermined angle or so as to fall within a predetermined range. Here, the reflection angle θ is set to 45 degrees, at which no loss occurs in a mode conversion from a shear wave to a longitudinal wave, or to any value within the range from about 35 to 55 degrees.

Not only the incident angle α, but also the inclination γ (the angle, as viewed in the depth direction of the rotor shaft 1, between a line joining the incident point P1 at which an ultrasonic beam is incident on the outer peripheral surface of the rotor shaft 1 and the reflection point at the flaw K and an axial line joining the incident point P1 and a point P2 where a normal to the surface of the slot dovetail portion 3 at the reflection point at the flaw K crosses the outer peripheral surface of the rotor shaft 1, that is, the inclination as viewed from the upper part of the shear-wave angle ultrasonic probe 21) is adjusted on the basis of the reflection angle θ. Thus, a flaw 6 can be accurately detected by performing forward, backward, rightward, and leftward scanning with oscillating scanning of the shear-wave angle ultrasonic probe 21 minimized.

The parameters have relationships expressed by Calculation Formulae (4) to (6).

$$\alpha = \sin^{-1}\left(\frac{2730}{3230}\sqrt{1-\sin^2\phi\cos^2\theta}\right) \quad (4)$$

$$\beta = \cos^{-1}(\sin\phi\ \cos\theta) \quad (5)$$

$$\gamma = \cos^{-1}\left(\frac{\sin\theta}{\sqrt{1-\sin^2\phi\cos^2\theta}}\right) \quad (6)$$

On the basis of these calculation formulae, the incident angle α, the refraction angle β, and the inclination γ can be determined from the slot angle φ, determined in the slot angle determination S1, described above, and the determined reflection angle θ. Consequently, on the basis of these angles, the shear-wave angle ultrasonic probe 21 can be optimally selected and set.

The parameters also have relationships expressed by Calculation Formulae (7) to (9).

$$X = Z \times \tan\beta \times \cos\gamma \quad (7)$$

$$Y = Z \times \tan\beta \times \sin\gamma \quad (8)$$

$$L = Z/\cos\beta \quad (9)$$

These calculation formulae allow the determination of the various dimensions between the shear-wave angle ultrasonic probe 21 and the flaw K.

Figure 13:
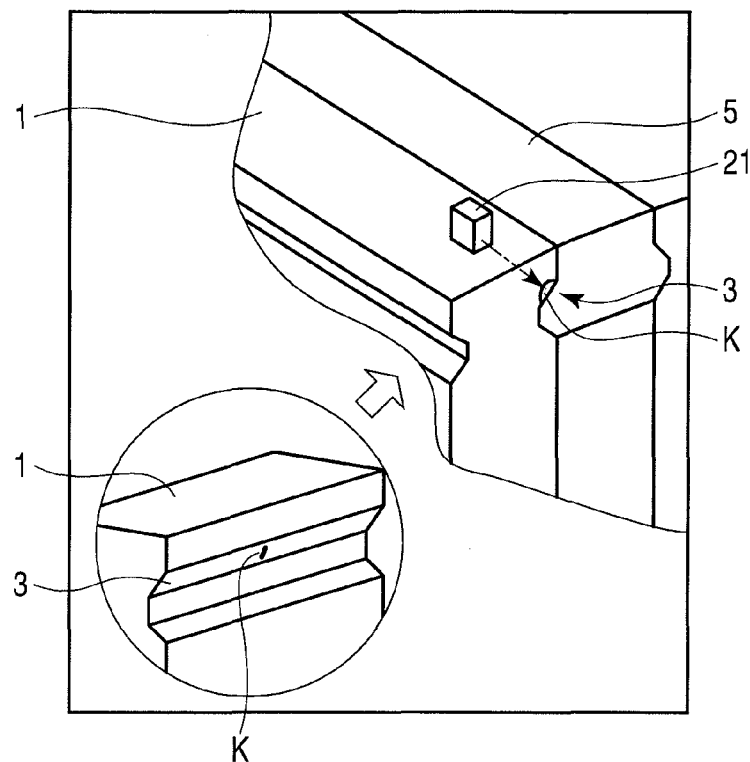
FIG. 13 is a diagram showing flaw detection performed by optimally selecting or setting the shear-wave angle ultrasonic probe 21.

FIG. 13 is a diagram showing flaw detection performed by optimally selecting or setting the shear-wave angle ultrasonic probe 21.

As shown in FIG. 13, a flaw in the slot dovetail portion 3 is detected using the shear-wave angle probe 21, installed on the outer peripheral surface of the rotor shaft 1. The size or the like of the detected flaw K is observed using the ultrasonic flaw detector 100.

Figure 14:
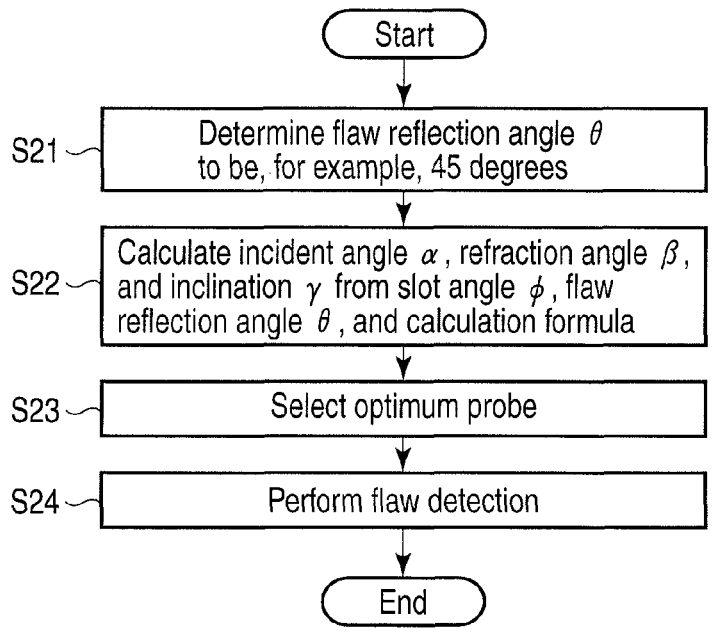
FIG. 14 is a flowchart showing the details of the process procedure of the slot dovetail portion flaw detection S2.

Now, the process procedure of the slot dovetail portion flaw detection S2 will be described with reference to FIG. 14.

First, the reflection angle θ at the flaw K is set to 45 degrees, at which no loss occurs in a mode conversion from a shear wave to a longitudinal wave, or to any value within the range from about 35 to 55 degrees (step S21).

Then, the incident angle α, the refraction angle β, and the inclination γ are determined from the slot angle φ, determined in the slot angle determination S1, described above, the determined reflection angle θ, and Calculation Formulae (4) to (6) (step S22).

Then, the shear-wave angle ultrasonic probe 21 is optimally selected or set on the basis of the incident angle α, the refraction angle β, and the inclination γ (step S23).

Finally, the optimally selected and set shear-wave angle ultrasonic probe 21 detects a flaw in the slot dovetail portion 3 (step S24). The flaw detection allows the flaw K to be detected, with the size or the like of the flaw K observed on the screen of the ultrasonic flaw detector 100.

Figure 15:
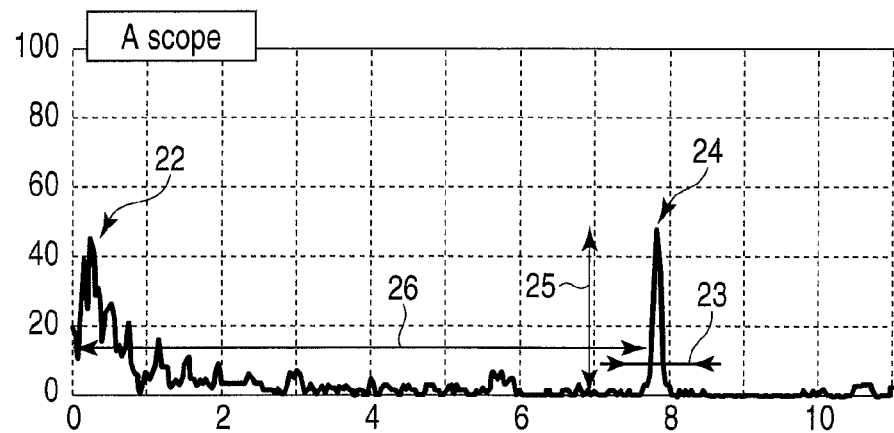
FIG. 15 is a diagram showing a waveform obtained on the screen of the ultrasonic flaw detector 100 during the slot dovetail portion flaw detection S2.

For example, such a waveform as shown in FIG. 15 is obtained on the screen of the ultrasonic flaw detector 100 in an A scope (the axis of abscissa: time or distance, the axis of ordinate: echo height). That is, a transmission wave 22 appears and is followed by a period 26 corresponding to the beam path length L. The period 26 is followed by a period 23 in which a reflection echo from the flaw K in the slot dovetail portion 3 appears. Then, the height 25 of a peak 24 during the period 23 is determined. On the basis of the height 25, the size of the flaw K can be determined.

Figure 16:
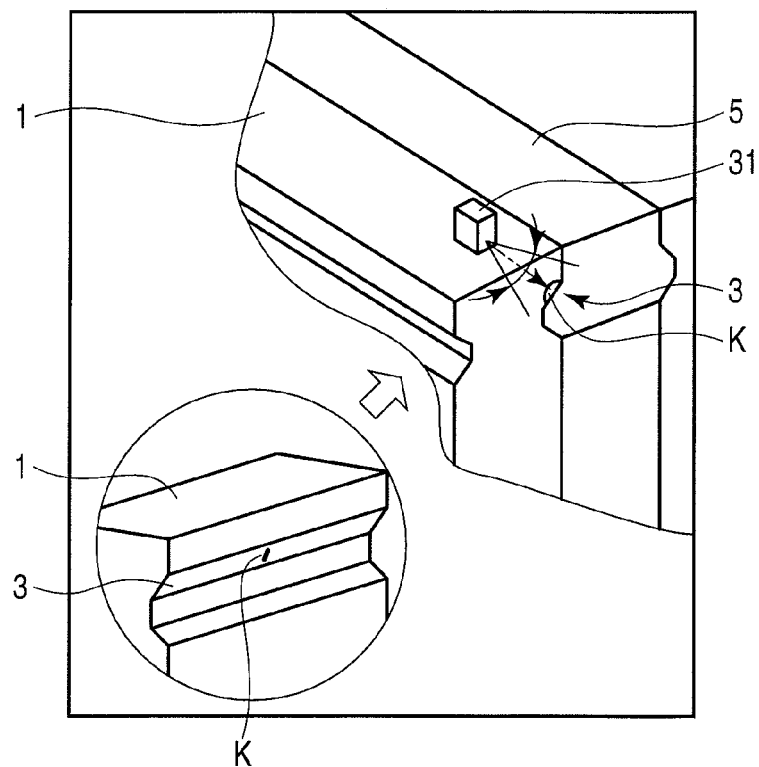
FIG. 16 is a diagram showing flaw detection performed on the slot dovetail portion 3 using a phased array probe 31.
Figure 19:
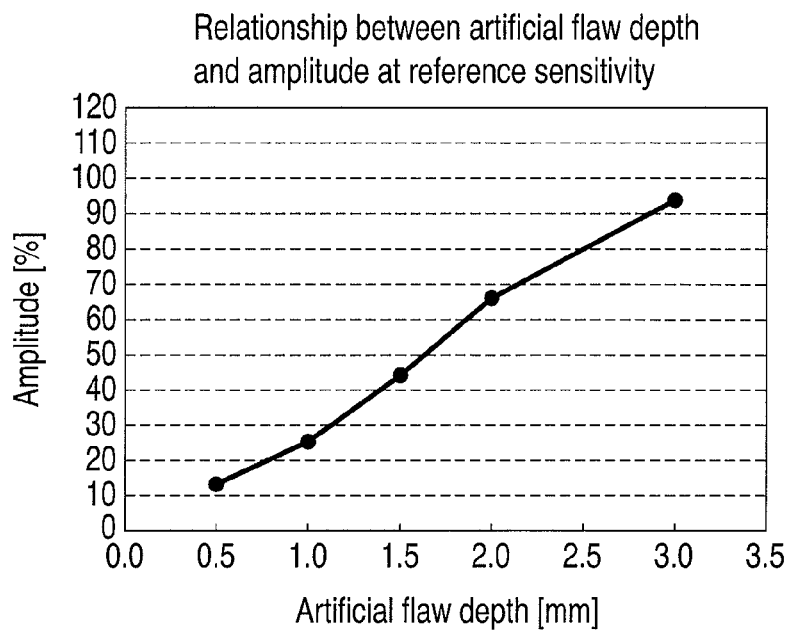
FIG. 19 is a diagram showing an example of data showing the relationship between an artificial flaw depth and an amplitude at a reference sensitivity.

The example has been illustrated in which the shear-wave ultrasonic probe 21 is used to detect a flaw in the slot dovetail portion 3. Alternatively, as shown in FIG. 16, a phased array probe 31 may be used to detect a flaw in the slot dovetail portion 3.

In this case, a flaw in the slot dovetail portion 3 is detected by performing scanning (sectorial scan) such that an ultrasonic beam is oscillated so as to vary the refraction angle β around the optimum reflection angle (θ=45 degrees) with the inclination γ shown in FIG. 10 fixed.

At this time, as shown in FIG. 17, a waveform and a sectorial flaw detection image (sectional image) are obtained on the screen of the ultrasonic flaw detector 100; the waveform is displayed in the A scope and contains a reflection echo 32 from the flaw K, and the sectorial flaw detection image is displayed in a B(D) scope and contains a shadow of the flaw K within the scan range around an ultrasonic beam 33. These images also enable the size of the flaw K to be determined.

(Flaw Depth Measurement)

The flaw depth measurement S3 will be described with reference to FIGS. 18 to 23.

FIG. 18 is a diagram illustrating the flaw depth from the surface of the slot dovetail portion 3. The flaw depth D corresponds to the length of the flaw K in a direction perpendicular to the surface of the slot dovetail portion 3.

If the flaw is small enough to inhibit the amplitude of the reflection echo from being saturated, the flaw depth D is determined by the amplitude method. In this case, data is used which indicates the "relationship between an artificial flaw depth and an amplitude at a reference sensitivity" such as the one shown in FIG. 19. The data is created as follows. The shear-wave angle ultrasonic probe 21 is used to set an echo from an artificial flaw of a known depth in a pre-created mockup test piece with a predetermined height (reference sensitivity) on the screen of the ultrasonic flaw detector 100. At the reference sensitivity, the heights (amplitudes) of echoes from artificial flaws of various depths are measured and recorded.

Figure 20:
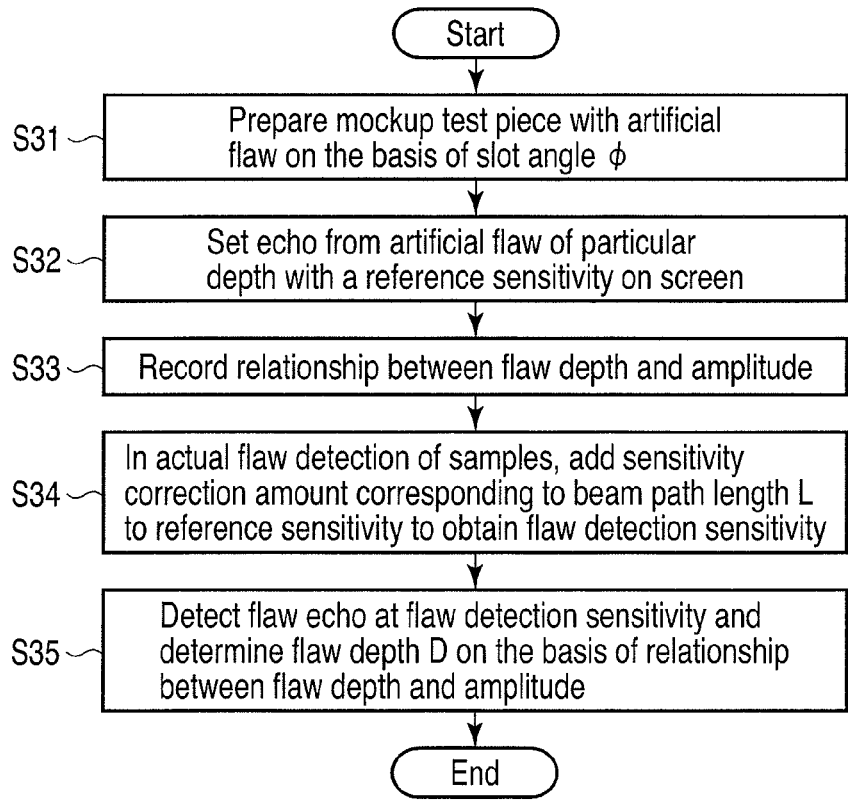
FIG. 20 is a flowchart showing the details of the process procedure of performing flaw depth measurement S3 by an amplitude method.

Now, the process procedure of performing the flaw depth measurement S3 by means of the amplitude method will be described with reference to FIG. 20.

First, a mockup test piece is prepared which has an artificial flaw of a known depth which is small enough to prevent the echo from being saturated, on the basis of the slot angle φ, determined in the slot angle determination S1 (step S31).

Then, an echo from an artificial flaw of a particular depth is set with a predetermined height (reference sensitivity) on the screen of the ultrasonic flaw detector 100 (step S32).

Then, at the reference sensitivity, the heights (amplitudes) of echoes from artificial flaws of various depths are measured and recorded to create data indicating the "relationship between the artificial flaw depth and amplitude at the reference sensitivity" (step S33).

Then, in an actual flaw detection on the slot dovetail portion 3, flaw detection sensitivity is set equal to the reference sensitivity plus a sensitivity correction amount based on a distance amplitude characteristic curve for the shear-wave angle probe 21 according to the beam path length L (step S34).

Finally, if a reflection echo from the flaw K is detected, the amplitude of the reflection echo is checked against the "relationship between the artificial flaw depth and amplitude at the reference sensitivity" to determine the flaw depth D.

Thus, using the amplitude method enables the depth of a small flaw in the slot dovetail portion 3 to be appropriately determined (step S35).

Figure 21:
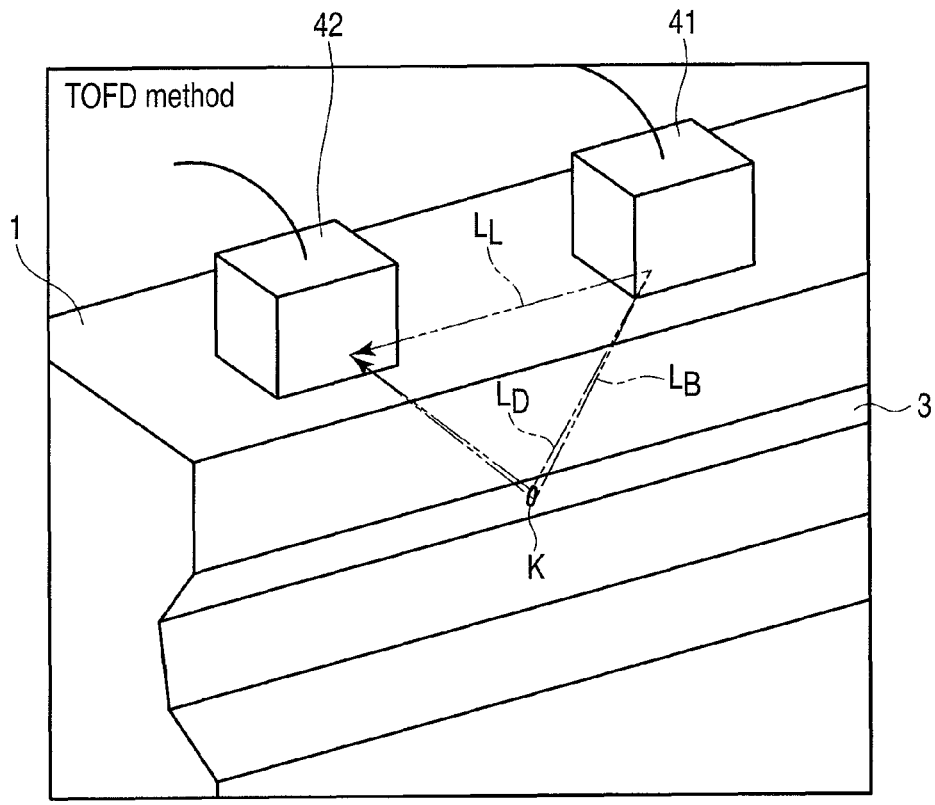
FIG. 21 is a diagram showing how to perform the flaw depth measurement S3 by a TOFD method.

On the other hand, if the flaw is so large that the amplitude of the reflection echo from the flaw 6 is saturated, the flaw depth D is determined by the TOFD method. In this case, as shown in FIG. 21, two longitudinal-wave angle ultrasonic probes 41 and 42 having the same refraction angle β and inclination γ as those of the shear-wave angle ultrasonic probe 21, described above, are arranged opposite each other on the surface of the rotor shaft 1. Furthermore, the TOFD method is applied. Then, the flaw depth D in the slot dovetail portion 3 is determined from the beam path length $L_L$ of a lateral wave, the beam path length $L_D$ of a diffracted wave, the beam path length $L_B$ of a back wall wave, and Calculation Formula (10).

$$D = \sqrt{\left(\frac{L_B}{2}\right)^2 - \left(\frac{L_L}{2}\right)^2} - \sqrt{\left(\frac{L_D}{2}\right)^2 - \left(\frac{L_L}{2}\right)^2} \tag{10}$$

Figure 22:
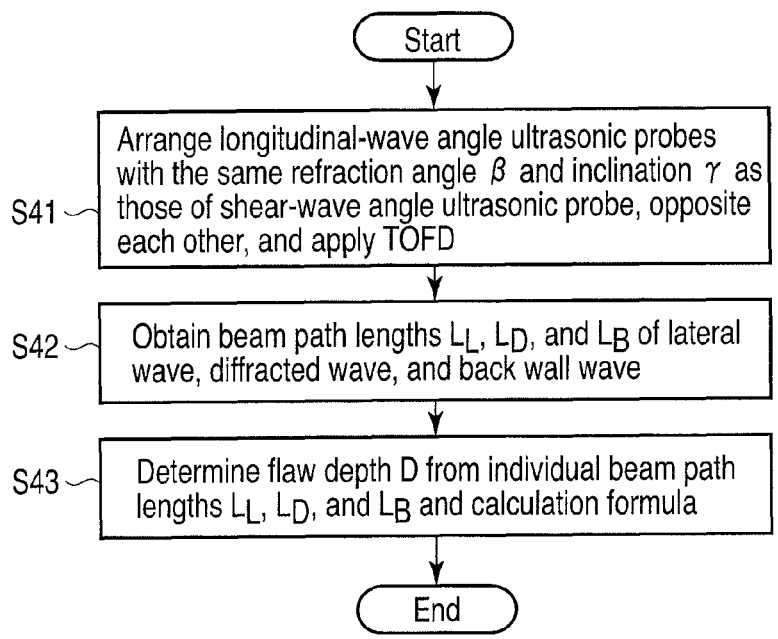
FIG. 22 is a flowchart showing the details of the process procedure of performing the flaw depth measurement S3 by the TOFD method.

Now, the process procedure of performing the flaw depth measurement S3 by means of TOFD will be described with reference to FIG. 22.

First, the two longitudinal-wave angle ultrasonic probes 41 and 42 having the same refraction angle β and inclination γ as those of the shear-wave angle ultrasonic probe 21, described above, are arranged opposite each other on the surface of the rotor shaft 1. Flaw detection is then performed on the basis of TOFD (step S41).

Figure 23:
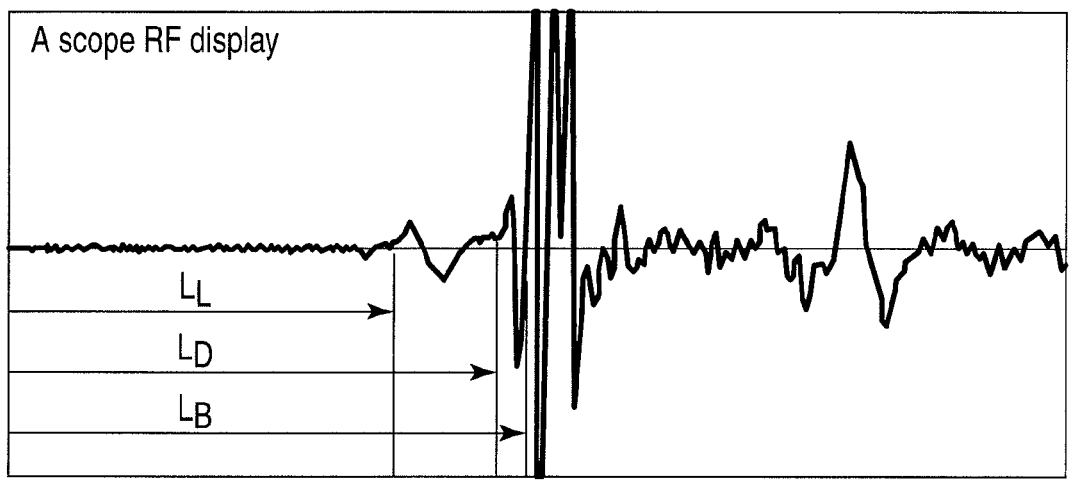
FIG. 23 is a diagram showing a waveform obtained on the screen of the ultrasonic flaw detector 100 during the flaw depth measurement S3 by the TOFD method.

Then, on the screen of the ultrasonic flaw detector 100, RF display in the A scope provides such a waveform as shown in FIG. 23. Thus, the beam path length $L_L$ of the lateral wave, the beam path length $L_D$ of the diffracted wave, and the beam path length $L_B$ of the back wall wave are obtained (step S42).

Finally, the flaw depth D is determined from the individual beam path lengths $L_L$, $L_D$, and $L_B$ and Calculation Formula (10).

Thus using TOFD method enables the depth of a large flaw in the slot dovetail portion 3 to be appropriately determined.

As described above in detail, the present embodiment allows ultrasonic testing to be efficiently carried out on the slot dovetail portion of the turbine generator rotor shaft through the slot angle determination S1, the slot dovetail portion flaw detection S2, and the flaw depth measurement S3.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A flaw detection testing method applied to a slot dovetail portion of a turbine generator rotor shaft, the method comprising:

an angle determining step of determining a slot angle of the slot dovetail portion using a variable-angle ultrasonic probe;

a flaw detection performing step of, on the basis of a determination result in the angle determining step, performing flaw detection to detect a flaw in the slot dovetail portion using an angle ultrasonic probe or a phased array probe; and a flaw depth measuring step of, when the flaw is detected in the flaw detection performing step, measuring a depth of the flaw from a surface of the slot dovetail portion using an angle ultrasonic probe.

2. The method according to claim 1, wherein the angle determining step comprises calculating the slot angle of the slot dovetail portion and the depth of the slot dovetail portion from an outer peripheral surface of the rotor shaft, on the basis of an ultrasonic incident angle and a beam path length at which a reflection echo corresponding to an ultrasonic beam which is emitted by a longitudinal-wave variable-angle ultrasonic probe installed on the outer peripheral surface of the rotor shaft and which is then reflected by the slot dovetail portion has the maximum amplitude.

3. The method according to claim 1, wherein the flaw detection performing step comprises adjusting a reflection angle at which an ultrasonic beam is reflected by the flaw to a predetermined angle or so as to fall within a predetermined range.

4. The method according to claim 3, wherein the flaw detection performing step comprises adjusting, not only the ultrasonic incident angle, but also an inclination corresponding to an angle, as viewed in a depth direction of the rotor shaft, between a line joining an incident point at which an ultrasonic beam is incident on the outer peripheral surface of the rotor shaft and a reflection point at the flaw and an axial line joining the incident point and a point where a normal to a surface of the slot dovetail portion at the reflection point at the flaw crosses the outer peripheral surface of the rotor shaft, on the basis of the reflection angle.

5. The method according to claim 1, wherein the flaw detection performing step comprises performing sectorial scan on the slot dovetail portion using a phased array probe.

6. The method according to claim 1, wherein the flaw depth measuring step comprises, when a size of the flaw detected in the flaw detection performing step is smaller than a preset value, measuring the depth of the flaw by an amplitude method utilizing a relationship between the depth of the flaw and an amplitude of a reflection echo from the flaw.

7. The method according to claim 1, wherein the flaw depth measuring step comprises, when a size of the flaw detected in the flaw detection performing step is equal to or greater than the preset value, measuring the depth of the flaw by a time of flight diffraction (TOFD) method.

* * * * *